United States Patent [19]

Hiismäki et al.

[11] Patent Number: 5,703,918
[45] Date of Patent: Dec. 30, 1997

[54] MODERATOR MATERIAL FOR NEUTRONS AND USE OF SAID MATERIAL

[75] Inventors: Pekka Hiismäki, Espoo; Iiro Auterinen, Helsinki, both of Finland

[73] Assignee: Radtek Oy, Espoo, Finland

[21] Appl. No.: 571,892

[22] PCT Filed: May 24, 1994

[86] PCT No.: PCT/FI94/00206

§ 371 Date: Jun. 10, 1996

§ 102(e) Date: Jun. 10, 1996

[87] PCT Pub. No.: WO94/29881

PCT Pub. Date: Dec. 22, 1994

[30] Foreign Application Priority Data

Jun. 14, 1993 [FI] Finland ............................. 932711

[51] Int. Cl.$^6$ ............... G21C 5/00; G21K 1/00; A61N 5/10

[52] U.S. Cl. ............................. 376/458; 376/906; 428/650

[58] Field of Search ............................. 376/458, 287, 376/288, 906, 340, 346; 250/515.1, 518.1; 252/478; 428/650, 654; 420/528; 423/489

[56] References Cited

U.S. PATENT DOCUMENTS

| | | | |
|---|---|---|---|
| 3,995,163 | 11/1976 | Colditz | 250/506 |
| 4,362,696 | 12/1982 | Brehm, Jr. et al. | 376/457 |
| 4,566,989 | 1/1986 | Radford et al. | 252/478 |
| 4,675,150 | 6/1987 | Russell, Jr. et al. | 376/340 |
| 5,015,863 | 5/1991 | Takeshima et al. | 250/515.1 |

FOREIGN PATENT DOCUMENTS 2262379  9/1975  France.

*Primary Examiner*—Daniel D. Wasil
*Attorney, Agent, or Firm*—Steinberg, Raskin & Davidson, P.C.

[57] ABSTRACT

The invention concerns a moderator material used for moderation of high-velocity neutrons, in particular of fission neutrons, to epithermal neutrons. The principal components of the moderator material are aluminum fluoride and aluminum metal, which have been formed into a dense composite substantially free of pores, wherein the material contains 20 to 50%-vol. of aluminum metal and 80 to 50%-vol. of aluminum fluoride. Further, the use of the moderator material in accordance with the invention in neutron capture therapy of cancer tumours is described, such as in boron neutron capture therapy (BNCT).

12 Claims, 1 Drawing Sheet

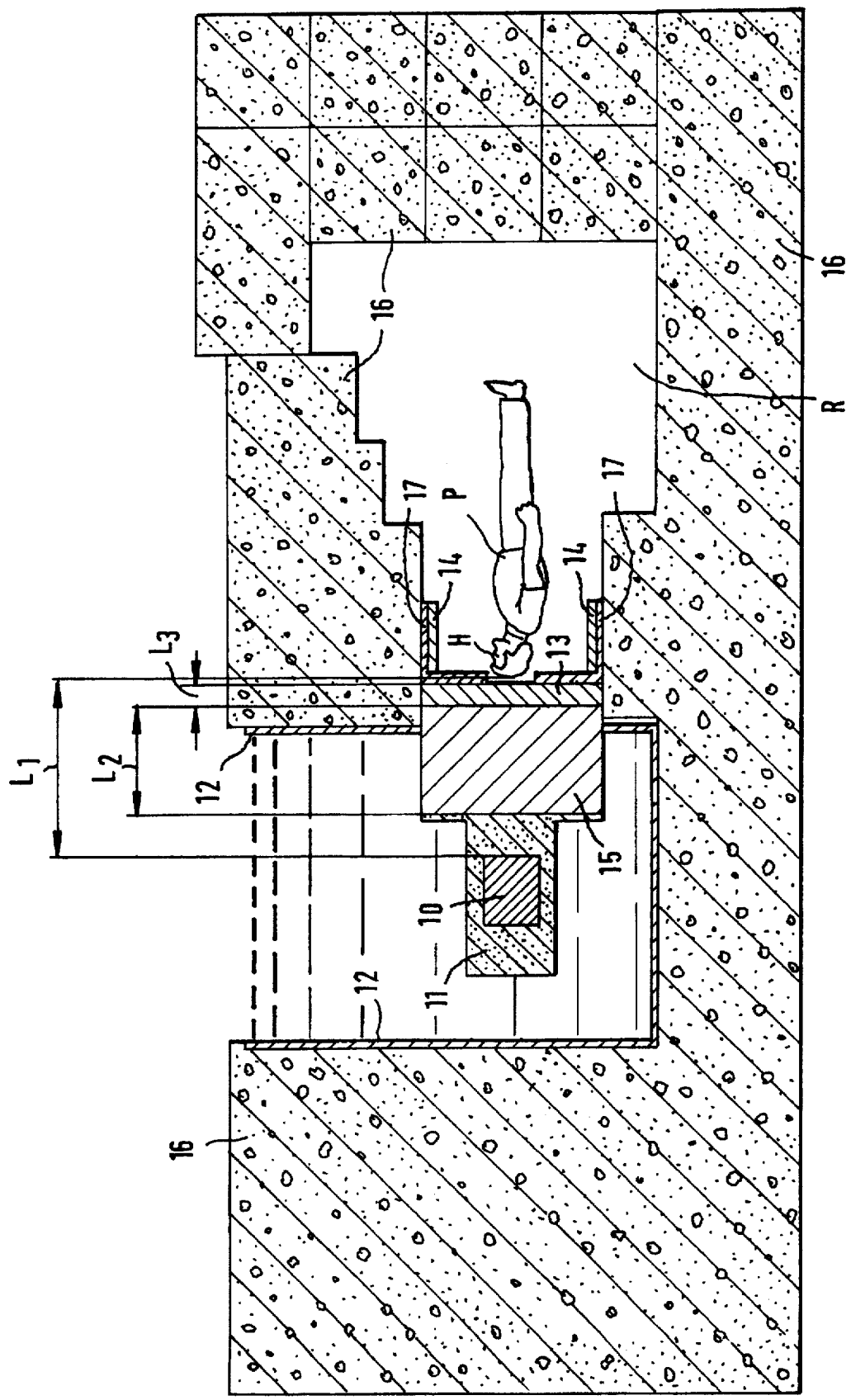

MODERATOR MATERIAL FOR NEUTRONS AND USE OF SAID MATERIAL

The invention concerns a moderator material used for moderation of high-velocity neutrons, in particular of fission neutrons, to epithermal neutrons.

Further, the invention concerns a novel use of the moderator material for neutrons in accordance with the invention.

With respect to the prior art related to the present invention, reference is made to the cited paper Proceedings of an International Workshop on Neutron Beam Design, Development, and Performance for Neutron Capture Therapy, held Mar. 29–31, 1989, at the Massachusetts Institute of Technology, in Cambridge, Mass., Edited by Otto K. Harling, John A. Bernard and Robert G. Zamenhof, Plenum Press, New York.

The boron neutron capture therapy (BNCT) is based thereon that, to the patient, through the blood circulation, an agent is administered that seeks its way into the cancer tissue and to whose molecule components have been attached that include boron atoms. A neutron flux is directed at the location of the cancer tissue, the neutrons in said neutron flux being absorbed into the boron and splitting the boron to lithium and helium, which destroy exactly cancer cells very locally, but which destroy any other tissue very little.

In BNCT, the formula of the boron neutron capture is as follows:

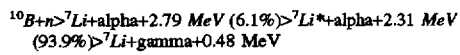

$$^{10}B+n \rightarrow {}^{7}Li+\text{alpha}+2.79 \text{ MeV } (6.1\%) \rightarrow {}^{7}Li^{*}+\text{alpha}+2.31 \text{ MeV}$$
$$(93.9\%) \rightarrow {}^{7}Li+\text{gamma}+0.48 \text{ MeV}$$

The boron neutron capture therapy produces quite a little strain on the patient. Surgical operation and anaesthesia are not needed. For the therapy team, the radiation strain does not differ in any way from administration of conventional radiological therapy.

In BNCT, slow or thermal neutrons have been used, whose depth of penetration is so little that the patient's cranium must be opened for the time of the therapy. On the contrary, epithermal neutrons of higher velocity are not moderated for capture by boron atoms until in the interior of the head, in which case the cranium does not have to be opened.

In boron neutron capture therapy, attempts are made to produce a distribution of the flux of thermal neutrons in the area of the body part to be treated, for example the head, which distribution of flux has a rather wide maximum sufficiently deep in the area to be treated. It is well known that this aim is reached best if epithermal neurons are passed from an external source to the body part to be treated, which neutrons are not thermalized until in the interior of the body. The neutron source best suitable for the therapy purpose is a research reactor, which produces primarily high-velocity fission neutrons. They must be moderated under control to epithermal neutrons, to the energy range of 1 eV . . . 10 keV, so that the proportion of high-velocity neutrons remains sufficiently low. As is known from prior art, many different materials have been suggested for the moderator material, such as metallic aluminum, aluminum oxide, aluminum fluoride, silicon, and equivalent.

Aluminum fluoride is a subliming compound, which is available as a porous powder, but out of it, it is impossible to prepare a dense material free of pores. Porosity is a drawback in principle, for it increases the necessary material thickness and brings the treatment point unduly far from the primary source, thereby lowering the useful intensity that can be achieved.

The object of the present invention is to provide a novel moderator material for neutrons by whose means the above drawbacks can be eliminated.

In view of achieving the objectives stated above and those that will come out later, the moderator material in accordance with the invention is mainly characterized in that the principal components of the moderator material are aluminum fluoride and aluminum metal, which have been formed into a dense composite substantially free of pores.

According to the present invention, the moderator material defined above is used in boron neutron capture therapy (BNCT) of cancer tissues.

In the following, the invention will be described in detail with reference to the schematic illustration in the accompanying drawing, which is an illustration of principle of BNCT therapy by means of a research reactor.

In the FIGURE, a research reactor is shown as used in BNCT therapy. In a way in itself known, the reactor comprises a reactor core 10, a graphite reflector 11 surrounding said core, and a tank 12 with aluminum walls, which tank is filled with water. The BNCT station is constructed by replacing the graphite, which is placed around the reactor core 10 in a so-called thermal column, with a moderator material piece 15, which requires an epithermal beam and which is made of the material in accordance with the present invention, and with a gamma shield 13. The patient P, in whose head H the cancer tumour to be irradiated is placed, is surrounded by a lead shield 14 and by a deuterium/lithium epithermal-thermal neutron shield 17. The concrete frame of the reactor is denoted with the reference numeral 16. In order that the patient P could be placed in the neutron beam as freely as possible, the thermal column is widened in the horizontal direction by cutting the concrete wall of the reactor thinner. The radiation space R is lined with a gamma and neutron shield and isolated from the reactor hall by means of boronized heavy-concrete units.

According to calculations that have been made, an optimal moderator material for the moderator piece 15 is a material in which the atomic ratio of aluminum to fluorine is clearly higher than that in aluminum fluoride 1:3. This goal is achieved by preparing a composite in which the pores in aluminum fluoride are filled with aluminum metal. Alternatively, the moderator material may be a continuous network-formed matrix in which the remaining spaces are filled substantially completely by aluminum fluoride. The manufacture of the composite is carried out, for example, by means of the so-called HIP technique (HIP=hot isostatic pressing). If necessary, to the material, it is possible to add little amounts of a substance that absorbs thermal neutrons, such as lithium, for example in the form of lithium fluoride, if it is desirable to get rid of the component of thermal neutrons without formation of an intensive capture gamma source at the same time.

In a moderator material in accordance with the invention, the amount of aluminum is preferably 20 . . . 50%-vol. (percent by volume) and that of aluminum fluoride 80 . . . 50%-vol. With the above range of mixing ratio of aluminum to aluminum fluoride, in the moderator piece 15, out of the metallic aluminum, a unified and continuous, three-dimensionally network-formed matrix is formed, which keeps the moderator piece 15 together and in which the interior spaces are completely and densely filled with aluminum fluoride. The amount of lithium fluoride, which absorbs thermal neutrons, is preferably about 1%.

A moderator piece 15 that is made of a material in accordance with the invention has typically the dimensions 700×1000×1000 mm, of which the dimension $L_2$ indicated in the FIGURE is $L_2 \approx 700$ mm. The dimensions $L_1$ and $L_3$ indicated in the FIGURE are typically $L_1 \approx 1050$ mm and $L_3 \approx 1000$ mm.

In the following, the patent claims will be given, and the various details of the invention may show variation within the scope of the inventive idea defined in said claims and differ from what has been stated above by way of example only.

We claim:

1. Moderator material used for moderation of high-velocity neutrons to epithermal neutrons, said moderator material comprising aluminum fluoride and aluminum metal, as a composite substantially free of pores.

2. Moderator material as claimed in claim 1, wherein said material contains from about 20 to 50% by volume of aluminum metal and from about 80 to 50% by volume of aluminum fluoride.

3. Moderator material as claimed in claim 2, said moderator material further comprising a continuous three-dimensional, network-formed matrix of aluminum metal wherein the remaining spaces of said network are substantially filled by aluminum fluoride.

4. Moderator material as claimed in claim 1, further comprising a substance that absorbs thermal neutrons and that does not produce high energy gamma rays.

5. Moderator material as claimed in claim 1 wherein said high velocity neutrons comprising fission neutrons.

6. Moderator material as claimed in claim 4, said substance comprising lithium fluoride.

7. Moderator material as claimed in claim 6, said lithium fluoride added to the moderator material in the amount of about 1% by volume.

8. Moderator material as claimed in claim 1, wherein said atomic ratio of aluminum to fluorine is greater than 1 to 3.

9. Moderator material as claimed in claim 1, said material formed by a method of hot isostatic pressing.

10. A method of neutron capture therapy of cancer tumors comprising the steps of:

providing a neutron source having a moderator material as claimed in claim 1 around said source; and passing neutrons from the source through the moderator material into the body part of a patient to be treated, wherein said neutrons are not thermalized until in the interior of the body of the patient.

11. The method of claim 10 wherein said neutron capture therapy is boron neutron capture therapy.

12. The method of claim 10, wherein the neutron source is a research reactor which produces high-velocity fission neutrons, which are moderated under control to neutrons having an energy range of 1 eV to 10 keV.

* * * * *